United States Patent [19]

Sher et al.

[11] Patent Number: 5,566,576
[45] Date of Patent: Oct. 22, 1996

[54] UNIVERSAL SAMPLING DEVICE FOR HIGH AND LOW VISCOSITY SUBSTANCES

[75] Inventors: Samuel E. Sher, Rockaway; Stephen A. Borgianini, Mount Holly; Robert E. Carpenter, Nutley; Scott Santora, Hammonton; William S. Scavuzzo, Clark, all of N.J.

[73] Assignee: Norton Company, Worcester, Mass.

[21] Appl. No.: 252,516

[22] Filed: Jun. 1, 1994

Related U.S. Application Data

[62] Division of Ser. No. 939,341, Sep. 2, 1992, Pat. No. 5,349,875.

[51] Int. Cl.$^6$ ........................................ G01N 1/00
[52] U.S. Cl. .................... 73/864.65; 73/864.62; 73/864.63
[58] Field of Search ................. 73/864.51, 864.63, 73/864.73, 864.62, 864.65

[56] References Cited

U.S. PATENT DOCUMENTS

| | | | |
|---|---|---|---|
| 397,961 | 2/1889 | Bergmann | 73/864.63 |
| 4,406,171 | 9/1983 | Ueberschaer | 73/864.62 |
| 4,594,905 | 6/1986 | Roberts | 73/864.63 |
| 4,930,361 | 6/1990 | Nimberger | 73/864.62 |
| 4,991,434 | 2/1991 | Snow | 73/864.62 |
| 5,098,847 | 3/1992 | Welker | 73/864.62 |

Primary Examiner—Robert Raevis
Attorney, Agent, or Firm—Mary E. Porter; Brian Kolkowski; Stephen L. Borst

[57] ABSTRACT

A universal sampling device for retrieving samples of high and low viscosity substances at various depths and from specific portions of contained bodies of materials without being completely submerged therein, is disclosed. The sampling device is made of chemically inert material, has manually operable inlet and outlet vent valve means attached to opposite inlet and outlet ends of a relatively long tube into which the sample enters upon opening of the inlet and outlet valve means at the desired point in the substance to be tested. Means are provided for manually closing and opening of the inlet valve means such as pushing and pulling a valve stem by hand into sealingly engagement with an inlet valve body. Another method attaches a valve stem to an adjustable valve control rod extending upwardly through the tube and outlet valve means. Closing of the inlet valve means can be attained by pushing the device and valve stem against a bottom or side wall containing the substance until the inlet valve stem snaps closed prior to withdrawal of the device and sample therein. Means such as a manually operable piston and piston rod may be slidably inserted into the long tube for sucking samples of more viscous substance into the tube and for actuating the valve stem of the inlet valve means. Also provided are means attachable to the outlet vent valve means for allowing air to exhaust and enter the tube, secure and adjust the valve control and piston rods and for dispensing of the sample into open or sealed containers. Further provided is a coring type inlet valve for taking samples of more viscous substances such as thick sludge and mud.

1 Claim, 2 Drawing Sheets

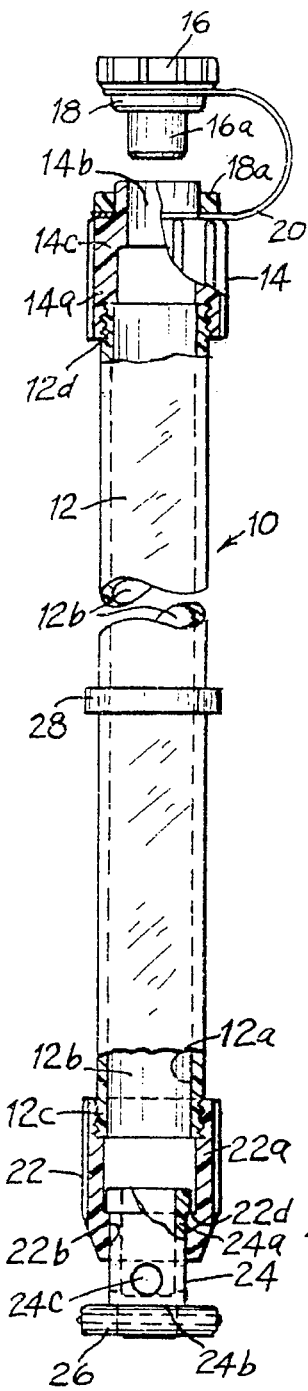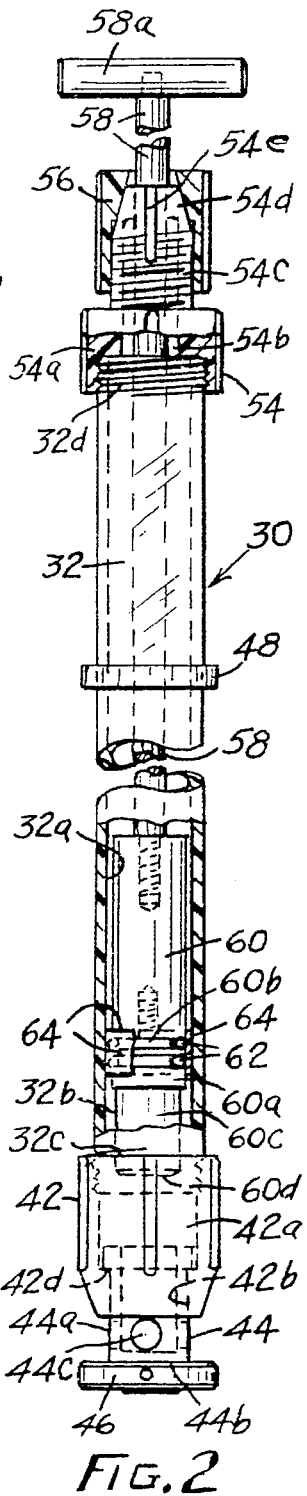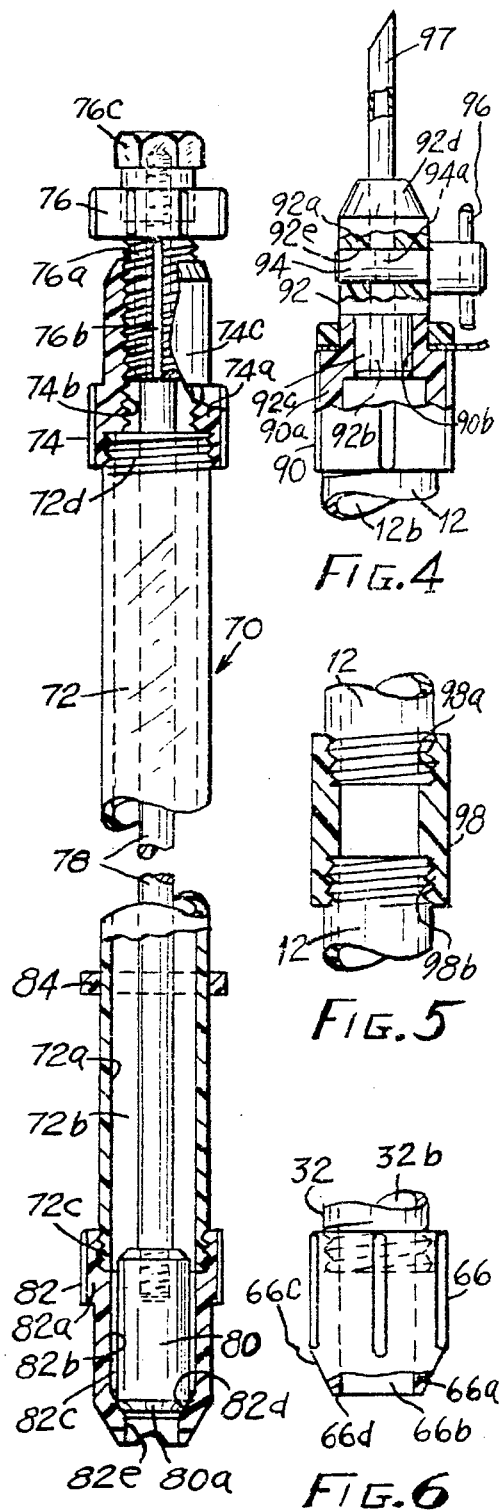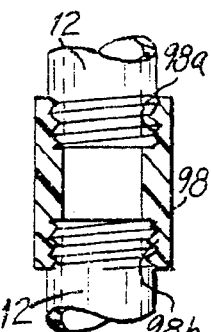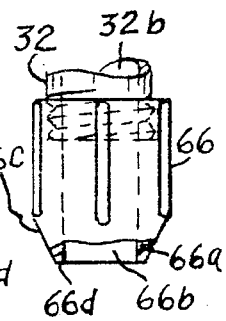

UNIVERSAL SAMPLING DEVICE FOR HIGH AND LOW VISCOSITY SUBSTANCES

This is a divisional of application Ser. No. 07/939,341, filed on Sep. 2, 1992, and issued as U.S. Pat. No. 5,349,875, on Sep. 27, 1994.

TECHNICAL DISCLOSURE

Relatively long and slender device for retrieving samples of high and low viscosity substances for analysis from various levels of virturally and contained source and particularly those stored in containers such as rail and truck tanks, cars, large tanks, vats, drums, and barrels having access openings therein of limited size.

BACKGROUND OF THE INVENTION

1. Field of the Invention

The invention relates to devices for retrieving samples of liquids, sludge, and mud, for analysis from virtually any source but particularly those stored in containers with limited access thereto.

2. Description of Prior Art

There is a need in commercial and scientific areas to obtain sample quantities of liquids, mixtures, slurries, etc.. Various tests are performed on the samples obtained, the results of which can be used for quality or production control or for monitoring the presence of toxic or other undesirable contaminates.

Samples must be gathered from many different locations such as 55 gallon drums, tank cars, vats, mixers, holding tanks, reservoirs, wells, streams, lakes, oceans, etc. Many devices are currently available for sampling purposes, but most are cumbersome to use and are limited to specific applications.

Heretofore, samples of materials to be analyzed for contaminants and toxins have been obtained by lowering and submerging a container such as a cylinder or bailer attached to a line or rod into a body of liquid, sludge, or mud to be tested. It is, however, difficult to direct and take samples at specific places and depths with a bailer since it begins to fill immediately upon entering the substance. Thus, the bailer may not contain a true sample of a specific area of especially viscous substances. Thereafter a valve at the bottom of the bailer or cylinder must automatically close upon retrieval of the sample contained therein to the surface.

Such devices are time consuming and are not well suited for retrieving samples of the more viscous liquids, sludges, and mud, stored or contained in tanks, drums, and barrels having openings of limited size and of greater depths.

The Applicant's device differs from prior art devices in that it has sufficient length to reach and take a sample at any point and depth. The device can be manually sealed prior to insertion into the source, opened at the desired point and depth, and manually sealed prior to withdrawal thereof to the surface. Also, it is of a size whereby it can pass through small openings of limited size usually found in drums, tanks and barrels containing the substance to be analyzed.

The Applicant's device also has interchangeable parts to deal with a wide range of viscosities and solid content. It is safer to use than the prior art devices as it minimizes operator contact with the substance being sampled and is faster and simpler to operate. Also the applicant's device allows easier repetition of accurate sampling at specific depths and can be made to have a translucent tubular body which allows visual inspection of the contents and through which immersible layers can be clearly seen. The device can be used for sampling virtually any chemical material.

SUMMARY OF THE INVENTION

A universal liquid and mud sampling device made of chemically inert materials includes an elongated tube or tubular cylinder with an outer wall surrounding an internal chamber extending between inlet and outlet ends thereof. The outlet end is connected to removable outlet vent valve means which are operable to selectively open and close off the outlet end of the tube or cylinder. Removable intake valve means are connected to the inlet end portion of the tubular cylinder and includes a valve stem operable to selectively open and close off an inlet valve bore adjacent the tubular cylinder.

For retrieving more viscous liquids and mud samples the universal device is provided with outlet vent valve means having an adjustable collet with vent passages and through which extends and frictionally engages an elongated piston rod connected to a piston slidably mounted within the tubular cylinder and adapted for opening the inlet valve means and sucking the sample into the internal chamber.

The universal device is further provided with manually operable inlet valve control means for retrieving a sample from a specific point or place within the body of the contained substances. The valve control means comprises a valve control rod adjustably connected to and movable relative to an outlet end portion of the outlet vent valve means. The valve control rod extends through the tubular cylinder and is connected at its low end to a valve stem movable to selectively open and close an inlet valve bore in the inlet valve control means.

Further provided are coring means for taking samples of more viscous substances and comprises providing the intake valve means with a coring valve body having a larger internal inlet valve bore surrounded by a relatively thin wall easily forced into viscous substances.

A depth indicator and wiper ring may also be provided that is slidably mounted on and movable relative to the exterior surface of the long tube. Thus, a sample may be taken at any depth and the substances wiped off the long tube or cylinder.

The inlet valve means may have a valve stem including a lower foot for engaging the walls containing the substances being tested whereby the valve stem may be pushed upwardly into and close the inlet valve means to retain a sample taken into the internal chamber during retrieval to the surface.

BRIEF DESCRIPTION OF THE DRAWING

FIG. 1 is a view partly in section of the universal sampling device of the invention;

FIG. 2 is a view partly in section of the universal sampling device provided with manually operable piston means for drawing more viscous substances into the device;

FIG. 3 is a view partly in section of the universal device provided with inlet valve control means for enabling the taking of samples at any point in a contained substance;

FIG. 4 is a view of an outlet-vent valve means provided with a removable adjustable valve connected to the upper end of the universal sampling device, FIG. 5 is a partial view of a pair of tubular cylinders of a universal sampling device connected by a coupling to increase the length thereof;

FIG. 6 is a view of inlet valve means adapted with coring means about the inlet valve bore thereof, attached to the lower end of a tubular cylinder.

DESCRIPTION OF THE PREFERRED EMBODIMENT(S)

Figure 7:
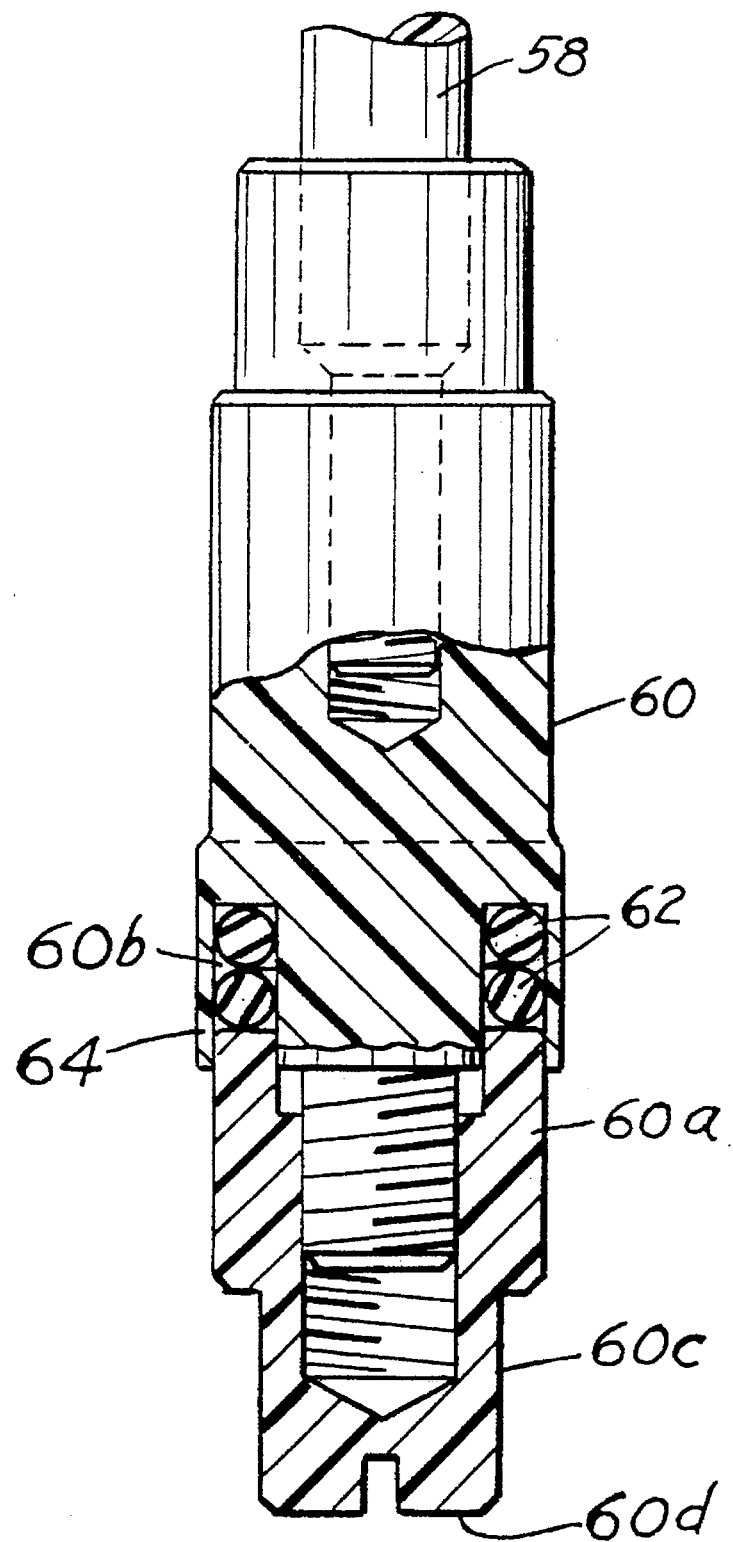
FIG. 7 is an enlarged view partly in section of a piston assembly for use with the device of FIG. 2.

Referring to FIG. 1 there is shown a basic or universal sampling device 10 comprising a relatively long and narrow tube or tubular cylinder 12 having an outer wall with internal surfaces 12a surrounding an internal chamber 12b and extending between opposite externally threaded lower inlet and upper outlet end portions 12c and 12d respectively. The tube is preferably made of a chemically inert translucent polypropylene or fluoropolymer material about 1" (2.54 cm) in width or diameter by 40" (1.01 m) in length and which can be coupled to other elongated tubes and thereby enables the device 10 to take samples of high and low viscosity substances, at any depth, from virtually any source contained by the bottom and sides of rivers or streams, lakes, reservoirs, lagoons, truck and rail tank cars, tanks, and drums, without being completely submerged therein. The universal device is particularly suited and sized to pass through the access opening in tanks and drums having bottom walls and side walls of measurably predetermined depth. Hence, the universal device may have a maximum diameter of from 1" to 3" (2.54 to 7.62 cm) and be 3 to 12 feet (0.9 to 3.6 m) in length.

Outlet vent valve means 14 are sealingly connected to the outlet end portion 12d of the tubular cylinder and comprise an outlet vent valve body 14a threaded at its lower inlet end to the outlet end portion 12d and has an internal outlet vent valve bore 14b extending through an opposite outlet end portion 14c.

An outlet vent valve plug 16 has a portion 16a insertable into and out of sealing engagement with the internal surface of the internal outlet vent valve bore 14b and by which the outlet end of the tubular cylinder and the outlet vent valve may be selectively manually opened or closed. A pair of retainer rings or washers 18 and 18a and a tether 20 connects the outlet valve vent plug 16 to the outlet end portion 14c of the outlet vent valve body 14a.

To the opposite lower inlet end portion 12c of the long tube 12 is sealingly connected inlet valve means 22 which includes an inlet valve body 22a threadably connected at an upper end to portion 12c, and an internal inlet valve bore 22b and internal surface at its opposite lower inlet portion sealingly engaging a manually movable inlet valve stem 24 slidably mounted therein. The inlet valve stem 24 has an internal passage surrounded by a side wall 24a extending upwardly from a bottom or lower wall portion 24b and inlet valve ports 24c situated in the sidewall 24a adjacent the bottom wall portion 24b. In the open position of the inlet valve means, the valve stem 24 is manually pushed or pulled outwardly to expose and position the inlet valve ports 24c beyond and outside of the lower inlet end of the inlet valve body 22 and valve bore 22b therein. To close, the inlet valve stem 24 and inlet ports are manually pushed upwardly into the inlet valve body 22a and sealed off by the engaging internal surface about the inlet valve bore 22b. Actuating means including a foot 26 is attached to the lower end of valve stem 24 for manually pulling the valve stem outwardly until it contacts a shoulder or stop 22d in the inlet valve body 22a and for pushing the valve stem 24 inwardly or upwardly to the closed position. A depth indicator and wiper ring 28 is slidably mounted on the exterior surface of the tubular cylinder 12.

The sampling device 10 is prepared for retrieving a sample at a predetermined depth by first pulling out the inlet valve stem 24 and inlet ports 24c to the open position. The depth indicator and wiper ring 28 is then moved the distance from the foot 26 of the inlet valve stem 24 at which the sample is to be taken below the surface of the contained substance. The inlet end portion of device 10 is then inserted into the liquid or substance until the depth indicator ring is at the surface of the contained substance whereupon outlet vent valve plug 16 is removed to allow air to vent from the tube 12 and the substance to enter the inlet valve means 22 and fill the internal chamber to the indicator ring 28. When filled to the desired level of the indicator ring the outlet vent valve plug 16 is inserted to close off the outlet vent valve means. Then the device is pushed downwardly or sidewardly until the foot 26 contacts either a side or bottom containing wall and forces the inlet valve stem upwardly to close off the inlet valve means and retain the sample in the internal chamber.

The device 10 is then lifted out of the contained substance and the depth indicator and wiper ring is moved along the tubular cylinder to wipe the substance therefrom.

Dispensing of the sample is done by either opening the inlet valve means or the outlet vent valve means and allowing the sample to drain into a separate container.

Another universal sampling device 30 for retrieving more viscous substances is shown in FIG. 2. The sampling device 30 is a modification of the device 10 shown in FIG. 1 and has a long tubular cylinder 32, including an outer wall 32a with an internal surface surrounding an internal chamber 32b and extending between lower inlet and upper outlet end portions 32c and 32d. The tube or cylinder 32 is substantially identical in construction and operation to the tube 12 described hereinabove and its lower end portion 32a is similarly connected to inlet valve means 42 substantially identical in construction and operation to the valve means 22 shown in FIG. 1. The inlet valve means 42 comprises an inlet valve body 42a threadably connected to portion 32c and an internal inlet valve bore 42b with internal surfaces sealingly engaging a manually movable inlet valve stem 44 slidably mounted therein.

The inlet valve stem 44 has an internal passage surrounded by a sidewall 44a extending upwardly from a bottom wall 44b and inlet valve ports 44c situated in the side wall adjacent the bottom wall 44b attached to a foot 46 for actuating the inlet valve stem 44 as described above in conjunction with the inlet valve means 22. A depth indicator and wiper ring 48 is slidably mounted on the exterior of the long tube 32.

Outlet vent valve means 54 sealingly attached to the upper outlet end 32d of the tubular cylinder 32 comprises an outlet vent valve body 54a threaded to the outlet end portion 32d and has an outlet vent valve bore 54b extending through an opposite outlet end portion 54c with external threads thereon. The outlet end portion 54c has an inwardly tapered chuck or collet end portion 54d with air vent slots 54e therein engaged by the internal mating tapered surfaces of an internally threaded adjustable chuck or collet nut 56. Adjusting the tapered collet nut 56 relative to the tapered collet end portion 54d causes the internal surfaces about an upper outlet end thereof to move into and out of frictional engagement with a piston rod 58 extending therethrough. Thus, the amount of frictional engagement with the piston rod 58 may be varied to either allow or restrict relative movement therebetween. The piston rod 58 extends from an upper end connected to an actuating handle 58a, through the collet end portion 54d, and internal bore 54b of the outlet vent valve body 54a and into the internal chamber 32b to its lower end connected to the upper end of a piston 60 slidably mounted within the internal chamber 32b of the tubular cylinder 32.

The piston 60 has a lower portion adjustably fastened thereto and at least one annular chamber or groove 60b into which is inserted at least one but preferably two elastic or resilient O-rings 62. Surrounding the annular chamber 60b and O-rings 62 is a thin flexible wall or piston ring 64 that is forced outwardly and expanded by the O-rings 62 into sealing engagement with the internal wall surface 32a of the tubular cylinder 32.

The O-rings 62 are made of resilient material and are expanded radially by engagement of the opposing shoulders of the piston 60 upon fastening of the lower portion 60a to the upper portion of the piston 60.

The thin flexible wall or piston ring may be made as a separate or an integral part of the piston and made of chemically inert fluoropolymer material about ¹⁄₃₂" (0.8 mm) thick by ¾" (19 mm) in diameter and ⅜" (9 mm) in width or height.

As shown in FIG. 7, the thin flexible wall or piston ring 64 is preferably an integral part of the piston 60 and surrounds the annular chamber and O-rings 62 situated therein. Inserted into the annular chamber 60b and engaging the O-rings 62 is an upper shoulder portion of the lower portion 60a of the piston. The upper shouldered portion of 60a is adjustably screw threaded to the piston 60 and thereby can be moved axially to increase or decrease the compressive force against the resilient O-rings. Thus, the O-rings and the flexible wall 64 can be expanded to take up for wear between the tubular cylinder and the piston ring.

The lower end portion 60a of the piston 60 has a reduced diameter 60c and extends to a lower end surface 60d which is adapted to engage the upper end of the valve stem 44 and force the valve stem to the open position shown.

Using the device 30 for retrieving a sample of viscous substance you first loosen the collect nut 56 and push the piston rod and piston 60 to a bottom position adjacent the inlet valve means 42 and move depth indicator ring 48 to desired position on tubular cylinder 32. The inlet valve stem 44 is then pushed upwardly to close the inlet valve means 42. The device 30 is then inserted into the substance to the desired depth indicated by the depth indicator ring 48, whereupon handle 58a, piston rod 58 and piston 60 are pushed further downwardly to contact and push the valve stem 44 downwardly to the open position. The handle 58a, piston rod 58, and piston 60, are pulled upwardly whereby the more viscous material, such as mud, is sucked into the internal chamber 32b while air vents out slots 54e. When the desired amount of substance is obtained in the tubular cylinder, the device and foot 46 is pushed against the bottom or side wall containing the substance until the valve stem 44 is forced to the closed position. Tighten the collet nut 56 to prevent movement of the piston rod 58 and piston 60 and thus secure the sample in place.

Remove the sampling device 30 with the sample therein from the substance and wipe the excess substance from the tubular cylinder with the ring 48. The sample may be dispensed into a container by loosening the collet nut, opening the inlet valve 42 by pulling the valve stem 44 outwardly with either your hands, protected by gloves, or by using a tool, if necessary, and pushing the piston rod and piston downwardly to force the sample out the inlet valve means 42.

Alternatively, the device 30 maybe further utilized to retrieve relatively more viscous and thick substances by removing and replacing inlet valve means 42 with the inlet valve and core means 66 shown in FIG. 6. The inlet valve and coring means 66 comprises an inlet valve core body 66a threaded to the lower inlet end of the tubular cylinder 32 and has an internal inlet valve bore 66b of substantially the same internal diameter as that of the internal chamber 32b in the tubular cylinder and a tapered inlet end portion 66c with a relatively thin or narrow annular inlet coring end surface 66d. Retrieving a sample of sludge using the device 30 with inlet valve coring means 66 requires loosening the collet nut and pushing handle 58a, piston rod and piston 60, to bottom of tubular cylinder. Then push the device into the sludge whereupon the sludge enters the inlet valve and coring means and moves the piston 60 upwardly as it enters the tubular cylinder 32. When the desired amount of the sludge has entered the internal chamber 32b as indicated by the depth indicator and wiper ring 48 the collet nut 56 is tightened to secure the piston rod and piston 60 and sample in place. Then the device 30 is removed from the source, the collet nut 56 loosened, and the piston rod 58 and piston 60 pushed downward to force the sample out of the inlet valve and coring means 66 and into another container.

Still another sampling device 70 for taking and retrieving samples of high and low viscosity substances from a specific point or part of the contained substance is shown in FIG. 3.

The sampling device 70 likewise comprises a tubular cylinder 72 including an outer wall 72a extending around an internal chamber 72b and extending to opposite lower inlet and upper outlet threaded end portions 72c and 72d respectively. The device 70 has an outlet vent valve means 74 including an outlet vent valve body 74a threaded to and sealingly connected to the outlet end portion 72d of the tubular cylinder 72. The outlet vent valve body 74a has an internally threaded valve bore 74b extending through an outlet end portion 74c. Actuating means including an adjustable valve knob 76 with an externally threaded lower end portion 76a and vent slots 76b therein are threaded into the internally threaded valve bore 74b. The valve knob 76 is attached by means of a retainer nut 76c to the upper end portion of a valve control rod 78 extending downwardly through the outlet vent valve means 74 and the internal chamber 72b of the tubular cylinder 72. At its lower end the control rod 78 is connected to a movable valve stem 80 having a tapered mating end surface 80a which is movable by selectively adjusting the knob 76 and valve control rod 78 to open and close the inlet valve means 82. The inlet valve means 82 has an inlet valve body 82a sealingly connected to the threaded lower end portion 72c of the tubular cylinder 72 and a wall and internal surface 82b extending around an internal bore 82c. The internal bore 82c extends downwardly and tapers inwardly to provide a tapered valve seat surface 82d adapted for mating sealing engagement with the mating end surface 80a of the valve stem 80. The tapered valve seat 82d extends downwardly and inwardly to an inlet valve bore 82e of smaller diameter at the inlet end of the inlet valve body 82. Alternatively, the tapered valve seat 82d may be an annular flat seat contacted by a mating flat end surface on the valve stem 80 or any other suitable equivalent means which will effectively open and close the inlet valve means 82. A depth indicator and wiper ring 84 is also provided on the tubular cylinder 72 to take and retrieve a sample from a specific part or point of a contained substance with the sampling device 70.

To retrieve a sample you first must determine the point and depth at which you desire to take a sample from in the substance. Then slide the depth indicator and wiper ring 84 to the corresponding point and depth on the tubular cylinder 72. The inlet valve means 82 is closed by turning the valve knob 76, valve control rod 78, and valve stem 80 into sealing engagement with the valve seat 82d. You now insert the sampling device 70 into the contained substance to the desired level and point therein indicated by the depth indicator and wiper ring 84. At the desired depth and point, the valve knob 76 is unscrewed to withdraw the valve control rod 78 and lift the valve stem 80 off the valve seat 82d, and open the inlet valve means 82.

The substance from the desired place will enter and pass into the internal chamber 72b of the tubular cylinder 72 while air vents out the vent slots 76b. When the desired amount is obtained the inlet valve means 82 is closed by turning the knob in the opposite direction whereby the control rod 78 moves the valve stem 80 against the valve seat 82d. The device 70 is then withdrawn and the depth indicator and wiper ring 84 is moved to wipe excess substance from the translucent tubular cylinder.

The sample may then be dispensed into another container by turning the knob 76 and control rod 78 so as to withdraw the valve stem 80 away from the valve seat 82d and thereby open the inlet valve means 82 and allow the substance to drain therefrom and air to be drawn into the tubular cylinder by way of the vent slots 76b.

Another outlet vent valve means 90 shown in FIG. 4 which maybe substituted for the outlet vent valve means 14 shown in FIG. 1 provides a flow control valve means for controlling the amount and flow of the sample being dispensed from the internal chamber 12b of a tubular cylinder 12. The outlet vent valve means 90 comprises an outlet vent valve body 90a, similar to the outlet vent valve body 14a, connected to the upper outlet end portion 12d of the tubular cylinder 12 and having an internal outlet vent valve bore 90b extending through an outlet end portion thereof. A flow control valve 92 including a valve body 92a has an internal passage 92b extending from an inlet portion 92c inserted into and sealingly engaging the internal surfaces about the outlet vent valve bore 90b to an outlet end portion 92d of the valve body 92a and valve 92.

The valve body 92a has a valve stem bore 92e extending transversely to and intersecting the internal passage 92b and into which is slidably and sealingly mounted a movable valve stem 94 with a valve port 94a therein movable into and out of alignment with the internal outlet passage 92b. Hence the flow control valve 92 may be selectively opened and closed by moving or rotating the valve stem 94 and valve port 94a into and out of alignment with the passage 92b. The outer end portion of the valve stem 94 is provided with a cross handle 96 for manually actuating the valve 92 and indicating the position of the valve port 94a relative to the passage 92b. An outlet extension tube 97 may also be provided and inserted into the outlet end 92d of the valve body 92a and internal passage 92b for dispensing the sample into smaller containers. Thus, the device 10 with the outlet vent valve means 90 attached thereto is used in substantially the same manner to take a sample with the exception that the flow control valve 92 replaces the outlet vent valve plug 16 and controls the dispensing of the sample.

In FIG. 5 there is shown a coupling means including a coupling 98 with threaded end portions 98a and 98b for coupling a pair of tubular cylinders 12 together to provide a sampling device of greater length for taking samples at greater depths.

The various parts of the universal device disclosed herein above are preferably made of chemically inert materials such as stainless steel, polypropylene, and fluoropolymer materials selected from a group consisting of polytetrafluoroethylene, tetrafluoroethylene and combinations thereof. However, depending on what is being sampled, the device may be made of other materials and coated with polypropylene or polytetrafluoroethenes, which are immune to attack by the substances being retrieved.

Also, the elongated tube for containing the sample therein may be made translucent by utilizing materials selected from a group consisting of fluorinated ethylene propylene (FEP), perfluoroalkoxy (PFA), polyvinylidene fluoride (PVDF), and combinations thereof.

Alternatively, the samples taken by the device 10 may also be dispensed into sealable vials and transferred to a laboratory for analysis by removing the outlet vent valve plug 16 inserting and utilizing the transfer device disclosed in U.S. Pat. No. 4,823,623, incorporated herein by reference.

As many other embodiments of the invention disclosed hereinabove are possible it is to be understood that the invention includes all modifications and equivalents thereof falling within the scope of the appended claims.

We claim:

1. A device for retrieving samples of substances at various depths from source contained by bottom and side containing walls without complete submergence of the device in the substance comprising:

an elongated tube having an outer wall surrounding an internal chamber and extending between opposite inlet and outlet ends of the tube;

inlet valve means including an inlet valve body with an inlet valve bore therein connected to an inlet end portion of the tube and adapted for manual insertion into the substance and allowing the passage of a sample thereof into the internal chamber of the tube;

a piston slidably mounted in the internal chamber and sealingly engaging the internal surface of the outer wall of the tube;

a piston rod attached to and extending upwardly from the piston and slidable through the outlet end of the tube having an internal bore and surface extending around the piston rod and a vent passage for allowing passage of air into and out of the internal chamber above the piston;

adjustable collet means connected to the outlet end portion of the outlet vent valve means for frictionally engaging and securing the piston rod and attached piston; and means attached to the piston rod for actuating the piston and sucking a sample of the substance through the inlet valve means and into the internal chamber.

* * * * *